(12) United States Patent
Yaszemski et al.

(10) Patent No.: US 6,884,432 B2
(45) Date of Patent: Apr. 26, 2005

(54) BLEND, CROSS-LINKABLE POLY (PROPYLENE FUMARATE) FOR IMMOBILIZATION AND CONTROLLED DRUG DELIVERY

(75) Inventors: Michael J. Yaszemski, Rochester, MN (US); Bradford L. Currier, Rochester, MN (US); Lichun Lu, Rochester, MN (US); Xun Zhu, Rochester, MN (US); Esmaiel Jabbari, Rochester, MN (US); Diederik H. R. Kempen, Utrecht (NL)

(73) Assignee: Mayo Foundation for Medical Education and Research, Rochester, MN (US)

( * ) Notice: Subject to any disclaimer, the term of this patent is extended or adjusted under 35 U.S.C. 154(b) by 57 days.

(21) Appl. No.: 10/423,209

(22) Filed: Apr. 25, 2003

(65) Prior Publication Data

US 2004/0023028 A1 Feb. 5, 2004

Related U.S. Application Data

(60) Provisional application No. 60/375,453, filed on Apr. 25, 2002.

(51) Int. Cl.$^7$ .......................... A61K 9/60; B32B 27/00; C08F 20/00
(52) U.S. Cl. ................. 424/460; 525/444; 525/445; 525/450; 428/402.21; 428/402.24; 424/457; 424/462; 523/113; 523/115
(58) Field of Search ................. 525/444, 445, 525/450; 428/402.21, 402.24; 424/457, 460, 462; 523/113, 115

(56) References Cited

U.S. PATENT DOCUMENTS 4,954,298 A 9/1990 Yamamoto et al.
5,019,400 A 5/1991 Gombotz et al.
5,733,951 A 3/1998 Yaszemski et al.
6,124,373 A 9/2000 Peter et al.
6,228,117 B1 5/2001 De Bruijn et al.

(Continued)

FOREIGN PATENT DOCUMENTS

EP 442671 A2 8/1991

OTHER PUBLICATIONS

Ishaug et al. "Bone formation by three–dimensional stromal osteoblast culture in biodegradable polymer scaffolds," *J Biomed Mater Res.* 36(1): 17–28, 1997.

(Continued)

Primary Examiner—Samuel A. Acquah
(74) Attorney, Agent, or Firm—Quarles & Brady, LLP

(57) ABSTRACT

Microspheres for controlled release of a bioactive agent are disclosed, and in particular, blend, cross-linkable poly (propylene fumarate) for immobilization and controlled drug delivery. The microsphere includes poly(propylene fumarate), a polymeric material other than poly(propylene fumarate) (e.g., poly(lactic-co-glycolic acid)), and a bioactive agent. The bioactive agent is selected depending on the physiological effect desired. For example, in bone regeneration applications, the bioactive agent may be selected from osteoinductive agents, peptides, growth hormones, osteoconductive agents, cytokines and mixtures thereof. The bioactive agent is dispersed in the microsphere, the microsphere has a diameter in the range of 1 to 300 micrometers, the poly(propylene fumarate) and poly(lactic-co-glycolic acid) are distributed in the microsphere, and the microsphere releases the bioactive agent in a sustained manner after an initial burst release. The microspheres may be covalently attached to a poly(propylene fumarate) scaffold for tissue regeneration applications in which the bioactive agent is released from the scaffold.

27 Claims, 12 Drawing Sheets

U.S. PATENT DOCUMENTS

| | | |
|---|---|---|
| 6,241,771 B1 | 6/2001 | Gresser et al. |
| 6,306,821 B1 | 10/2001 | Mikos et al. |
| 6,346,274 B1 | 2/2002 | Koll et al. |
| 6,355,755 B1 | 3/2002 | Peter et al. |
| 6,384,105 B1 | 5/2002 | He et al. |
| 6,419,945 B1 | 7/2002 | Gresser et al. |
| 6,423,790 B1 | 7/2002 | He et al. |
| 6,541,022 B1 | 4/2003 | Murphy et al. |
| 6,548,002 B1 | 4/2003 | Gresser et al. |

OTHER PUBLICATIONS

Ishaug, et al., "Osteoblast function on synthetic biodegradable polymers.", *J Biomed Mater Res*, 28(12): 1445–53, 1994.

R.G. Payne, "Development of an injectable, in situ crosslinkable, degradable polymeric carrier for osteogenic cell populations." Ph.D. thesis, Rice University, Houston, Texas, USA, 2001.

Agrawal et al., "Biodegradable polymeric scaffolds for musculoskeletal tissue engineering.", *J Biomed Mater Res*, 55(2): 141–50, 2001.

Lu et al. "Controlled release of transforming growth factor β1 from biodegradable polymer microparticles", *J Biomed Mater Res*, 50(3): 440–51, 2000.

Lu et al., "TGF–β1 release from biodegradable polymer microparticles: its effect on marrow stromal osteoblast function",*J Bone Joint SurgAm*, 83–A (Suppl 1 (Pt2)):S82–91, 2001.

Oldham et al., "Biological activity of rhBMP–2 released from PLGA microspheres",*J Biomech Eng*, 122(3): 289–92, 2000.

Peter et al., "Effects of transforming growth factor β1 released from biodegradable polymer microparticles on marrow stromal osteoblasts cultured on poly(propylene fumarate) substrates."*J Biomed Mater Res*, 50(3): 452–62, 2000.

Peter et al., "Synthesis of poly(propylene fumarate) by acylation of propylene glycol in the presence of a proton scavenger.", *J Biomater Sci Polym Ed* 10:363–373, 1999.

Davis et al., "The preparation and characterization of poly-(lactic–co–glycolide) microparticles. I. Oil–in–water emulsion solvent evaporation.", *Int J Pharm.*, 1991;77:169–75.

Davis et al., "The preparation and characterization of poly-(lactic–co–glycolide) microparticles. II. The entrapment of a model protein using a (water in oil)–in–water emulsion solvent evaporation technique.", *Pharm Res*, 1993;10:362–8.

Crotts et al., "Preparation of porous and nonporous biodegradable polymeric hollow microspheres.", *J Control Rel.*, 1995;35:91–105.

Roy et al., "Indomethacin–loaded microspheres: design and preparation by a multiple–emulsification technique and their in vitro evaluation.", *Pharm Res.*, 1992;9:1132–6.

Yang et al., "Morphology, drug distribution, and in vitro release of biodegradable polymeric microspheres containing protein fabricated by double–emulsion solvent extraction/evaporation method.", *Biomaterials*, 2001;22:231–41.

Bodemeier, "Encapsulation of water soluble drugs by a solvent evaporation method. I. Effects of process and formulation variables on drug entrapment." *J. Microencapsulation* 1990;7(3):347–355.

Bodemeier et al., "Solvent selection in the preparation of poly(DL–lactide) microspheres prepared by the solvent evaporation method.", *Int. J. Pharm* 1988;43:179–186.

Schugens et al., "Effects of the emulsion stability on the morphology and porosity of semicrystalline poly L–lactide microspheres prepared by the W–O–W double emulsion–evaporation.", *J Controlled Release* 1994;32:161–176.

US 6,884,432 B2

BLEND, CROSS-LINKABLE POLY (PROPYLENE FUMARATE) FOR IMMOBILIZATION AND CONTROLLED DRUG DELIVERY

CROSS-REFERENCES TO RELATED APPLICATIONS

This application claims priority from U.S. Provisional Patent Application No. 60/375,453, filed Apr. 25, 2002.

STATEMENT REGARDING FEDERALLY SPONSORED RESEARCH

This work was supported by the National Institutes of Health through grant number R01-AR45871-02.

BACKGROUND OF THE INVENTION

1. Field of the Invention

This invention relates to microspheres for controlled release of a bioactive agent. In one form, the microspheres include poly(propylene fumarate), poly(lactic-co-glycolic acid)), and a bioactive agent. The microspheres may be covalently attached to a poly(propylene fumarate) scaffold for tissue regeneration applications in which the bioactive agent is controllably released from the scaffold.

2. Description of the Related Art

In the field of tissue engineering, biodegradable polymeric biomaterials can serve as a scaffold to provide mechanical support and a matrix for the ingrowth of new tissue. As new tissue forms on the scaffold, the biomaterial degrades until it is entirely dissolved. The degradation products are eliminated through the body's natural pathways, such as metabolic processes. One example of the use of such biomaterials is as a temporary bone replacement to replace or reconstruct all or a portion of a living bone. The bone tissue grows back into the pores of the polymeric implant and will gradually replace the entire implant as the polymeric implant itself is gradually degraded in the in vivo environment.

Poly(propylene fumarate) (PPF) is one polymer that has been employed as such a biomaterial. Poly(propylene fumarate) is an unsaturated linear polyester that degrades in the presence of water into propylene glycol and fumaric acid, degradation products that are easily cleared from the human body by normal metabolic processes. Because the fumarate double bonds in poly(propylene fumarate) are reactive and crosslink at low temperatures, poly(propylene fumarate) can be an effective in situ polymerizable biomaterial. The high mechanical strength of cured poly(propylene fumarate) matrices and their ability to be crosslinked in situ makes them especially suitable for orthopedic applications.

Several poly(propylene fumarate) formulation methods and tissue regeneration applications for poly(propylene fumarate) have been developed. U.S. Pat. Nos. 6,423,790, 6,384,105, 6,355,755, 6,306,821, 6,124,373 and 5,733,951 describe various synthesis methods and applications for poly(propylene fumarate). The disclosure of these patents and all other patents and publications mentioned herein are incorporated herein by reference. An injectable, in situ polymerizable, biodegradable poly(propylene fumarate) scaffold for bone regeneration has also been developed. See, Ishaug et al. "Bone formation by three-dimensional stromal osteoblast culture in biodegradable polymer scaffolds." *J Biomed Mater Res*, 36(1): 17–28, 1997; and Ishaug, et al., "Osteoblast function on synthetic biodegradable polymers.", *J Biomed Mater Res*, 28(12): 1445–53, 1994. The poly (propylene fumarate) scaffold can be shaped into the desired structure either in an ex vivo mold or in situ. Solid poly (propylene fumarate) hardens within 5–15 minutes to attain mechanical properties similar to cancellous bone (see, R. G. Payne, "Development of an injectable, in situ crosslinkable, degradable polymeric carrier for osteogenic cell populations." Ph.D. thesis, Rice University, Houston, Tex., USA, 2001).

Controlled release of bioactive molecules such as cytokines and growth factors has also become an important aspect of tissue engineering because it allows modulation of cellular function and tissue formation at the afflicted site (see, Agrawal et al., "Biodegradable polymeric scaffolds for musculoskeletal tissue engineering.", *J Biomed Mater Res*, 55(2): 141–50, 2001). The encapsulation of drugs, proteins and other bioactive molecules within degradable materials has long been known to be an effective way to control the release profile of the contained substance. More recently, microencapsulation has been found to have similar effects, and has been used for the controlled delivery of various drugs and active proteins.

A variety of methods is known by which compounds can be encapsulated in the form of microparticles. See, for example, U.S. Pat. Nos. 5,019,400 and 4,954,298 and European patent application EP 442671. In these methods, the material to be encapsulated (drugs or other active agents) is generally dissolved, dispersed, or emulsified, using stirrers, agitators, or other dynamic mixing techniques, in a solvent containing the polymeric material. Solvent is then removed from the microparticles and thereafter the microparticle product is obtained. Encapsulation techniques have been successfully applied to encapsulate growth factors such as transforming growth factor-beta (TGF-b), recombinant bone morphogenetic protein (rhBMP-2) and basic fibroblast growth factor (bFGF) in poly(lactic-co-glycolic acid) (PLGA) microspheres (see, Lu et al. "Controlled release of transforming growth factor beta 1 from biodegradable polymer microparticles", *J Biomed Mater Res*, 50(3): 440–51, 2000; Lu et al., "TGF-beta 1 release from biodegradable polymer microparticles: its effects on marrow stromal osteoblast function", *J Bone Joint Surg Am*, 83-A (Suppl 1 (Pt 2)): S82–91, 2001; Oldham et al., "Biological activity of rhBMP-2 released from PLGA microspheres", *J Biomech Eng*, 122(3): 289–92, 2000; and Peter et al., "Effects of transforming growth factor beta 1 released from biodegradable polymer microparticles on marrow stromal osteoblasts cultured on poly(propylene fumarate) substrates." *J Biomed Mater Res*, 50(3): 452–62, 2000).

The addition of growth factors within a poly(propylene fumarate) scaffold could result in a composite biomaterial that could serve both a structural role and a drug delivery role. For example, an injectable formulation consisting of poly(propylene fumarate) and growth factor-loaded microspheres could be used to fill bone defects. However, the most extensively studied bioabsorbable microsphere is made from poly(lactic-co-glycolic acid), and conventional poly(lactic-co-glycolic acid) microspheres would not be expected to attach to the wall of a poly(propylene fumarate) scaffold. As a result, the poly(lactic-co-glycolic acid) microspheres can migrate out of the scaffold. Due to the migration of the poly(lactic-co-glycolic acid) microspheres, the local sustained release of the protein is less controllable.

Therefore, there is a need for bioabsorbable microspheres that controllably release a bioactive agent and that can be attached to a scaffold for tissue regeneration such that the microspheres do not migrate out of the scaffold. Further, there is a need for a material that can be used to prepare a scaffold for tissue regeneration having attached microspheres that controllably release a bioactive agent. Also, there is a need for a scaffold for tissue regeneration that has attached microspheres which controllably release a bioactive agent and which do not migrate out of the scaffold.

SUMMARY OF THE INVENTION

The foregoing needs are met by a microsphere according to the invention for controlled release of a bioactive agent. The microsphere includes poly(propylene fumarate), a polymeric material other than poly(propylene fumarate), and a bioactive agent. Preferably, the polymeric material is poly(lactic-co-glycolic acid). The bioactive agent is selected depending on the physiological effect desired. For example, in bone regeneration applications, the bioactive agent may be selected from osteoinductive agents, peptides, growth hormones, osteoconductive agents, cytokines and mixtures thereof. The bioactive agent is uniformly or non-uniformly dispersed in the microsphere, the microsphere has a diameter in the range of 1 to 300 micrometers, the microsphere has a surface free from indentations and cracks, the poly(propylene fumarate) and poly(lactic-co-glycolic acid) are uniformly or non-uniformly distributed in the microsphere, and the microsphere releases the bioactive agent in a sustained manner (and most preferably linear manner) after an initial burst release.

Drug release using microspheres alone is not predictable enough in vivo due to the mobility of these microspheres when in contact with body fluids. One purpose of the invention is to covalently bond the microspheres to the biodegradable polymer scaffolds. To achieve covalent bonding, poly(propylene fumarate) is incorporated to form blend microspheres. The double bonds along the poly(propylene fumarate) chain provide sites of covalent linkage with a poly(propylene fumarate)-based scaffold.

The foregoing needs are further met by a crosslinkable, biodegradable material according to the invention. The material may be injected into a site in the body for in situ crosslinking and formation of a scaffold for tissue regeneration having attached microspheres that controllably release a bioactive agent. The material includes a first polymeric material; microspheres including the first polymeric material, a second polymeric material, and a bioactive agent; and a crosslinking agent for crosslinking the first polymeric material. In one form, the first polymeric material is poly(propylene fumarate), the second polymeric material is poly(lactic-co-glycolic acid), and the crosslinking agent is a free radical initiator. The double bonds along the poly(propylene fumarate) chain provide sites of crosslinking agent free radical initiated covalent linkage with the poly(propylene fumarate) in the microspheres. The bioactive agent is selected depending on the physiological effect desired. For example, in bone regeneration applications, the bioactive agent may be selected from osteoinductive agents, peptides, growth hormones, osteoconductive agents, cytokines and mixtures thereof. The bioactive agent is uniformly or non-uniformly dispersed in the microsphere, the microsphere has a diameter in the range of 1 to 300 micrometers, the microsphere has a surface free from indentations and cracks, the poly(propylene fumarate) and poly(lactic-co-glycolic acid) are uniformly or non-uniformly distributed in the microsphere, and the microsphere releases the bioactive agent in a sustained manner (and most preferably linear manner) after an initial burst release.

The foregoing needs are also met by a scaffold for tissue regeneration according to the invention. The scaffold includes a biodegradable matrix comprising a first polymeric material; and a microsphere including the first polymeric material, a second polymeric material, and a bioactive agent, wherein at least a portion of the first polymeric material in the matrix and at least a portion of the first polymeric material in the microsphere are crosslinked. In one form, the first polymeric material is poly(propylene fumarate), and the second polymeric material is poly(lactic-co-glycolic acid). The poly(propylene fumarate) matrix is covalently linked with at least a portion of the poly(propylene fumarate) in the microspheres. The bioactive agent is selected depending on the physiological effect desired. For example, in bone regeneration applications, the bioactive agent may be selected from osteoinductive agents, peptides, growth hormones, osteoconductive agents, cytokines and mixtures thereof. The bioactive agent is uniformly or non-uniformly dispersed in the microsphere, the microsphere has a diameter in the range of 1 to 300 micrometers, the microsphere has a surface free from indentations and cracks, the poly(propylene fumarate) and poly(lactic-co-glycolic acid) are uniformly or non-uniformly distributed in the microsphere, and the microsphere releases the bioactive agent in a sustained manner (and most preferably linear manner) after an initial burst release.

The scaffolds with covalently immobilized microspheres allow better control of the localization of these microspheres once implanted into the body. Bioactive molecules loaded into the microspheres have a more predictable release profile from such composite scaffolds. Moreover, the initial burst release is significantly reduced resulting in a more sustained release pattern.

It is thus an advantage of the present invention to provide composite microspheres blended from poly(propylene fumarate) and poly(lactic-co-glycolic acid). By blending poly(propylene fumarate) into poly(lactic-co-glycolic acid) microspheres, the carbon-carbon double bonds of poly(propylene fumarate) can be used for covalent immobilization of these microspheres to a poly(propylene fumarate) containing scaffold, thus coupling microsphere release with poly(propylene fumarate) scaffold degradation.

It is another advantage of the present invention to provide for the addition of growth factors within a poly(propylene fumarate) scaffold resulting in a composite biomaterial that could serve both a structural role and a drug delivery role. For example, an injectable formulation consisting of poly(propylene fumarate) and growth factor-loaded microspheres can be used to fill bone defects.

It is yet another advantage of the present invention to provide a method for fabricating poly(propylene fumarate)/poly(lactic-co-glycolic acid) blend microspheres with similar surface morphology, entrapment efficiency and size distribution as poly(lactic-co-glycolic acid) microspheres.

It is still another advantage of the present invention to provide a method for the addition of bioactive molecules, such as recombinant bone morphogenetic protein, to a tissue regeneration scaffold which results in a composite biomaterial that can be used as an alternative to bone graft for the treatment of skeletal defects. Encapsulation of these molecules within biodegradable microspheres allows for the controlled release of these bioactive substances at optimal levels at the site of healing.

It is yet another advantage of the present invention to provide a method for incorporation of bioactive molecules such as cytokines and growth factors and their controlled release from a poly(propylene fumarate)-based scaffold which allows for further modulation of cellular function and tissue formation at a treatment site. Such bioactive molecules can be encapsulated into biodegradable microspheres, which can then be impregnated into the scaffold.

These and other features, aspects, and advantages of the present invention will become better understood upon consideration of the following detailed description, drawings, and appended claims.

DETAILED DESCRIPTION OF THE INVENTION

Figure 1:
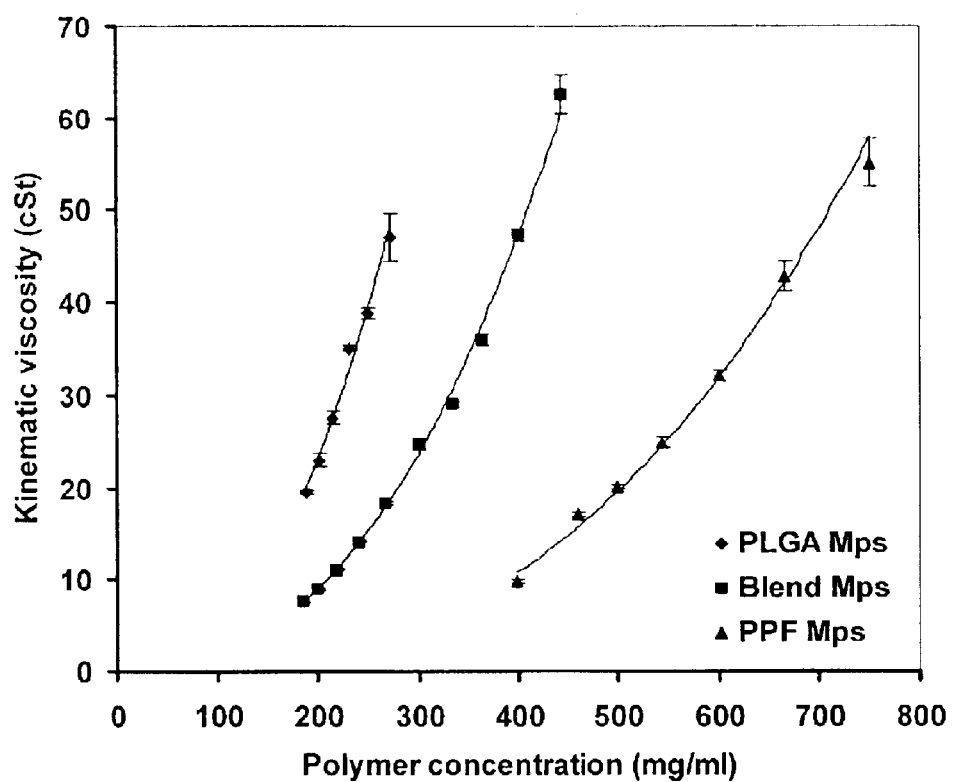
FIG. 1 shows the kinematic viscosity of pure PLGA (♦), a 50:50 ratio PPF/PLGA blend (■) and PPF (▼) solution in dichloromethane as a function of polymer concentration.

In a first aspect, the invention provides a microsphere for controlled release of a bioactive agent. The microsphere includes poly(propylene fumarate) (H—[—O—CH$_2$—CH(CH$_3$)—O—CO—CH=CH—CO—]$_n$—OH), a polymeric material other than poly(propylene fumarate), and a bioactive agent. Because poly(lactic-co-glycolic acid) has proven to be effective in controllably releasing a bioactive agent, it is preferred that the polymeric material is poly(lactic-co-glycolic acid) (H—[—OCHR—CO—]$_n$—OH, R=H, CH$_3$). The poly(propylene fumarate) and poly(lactic-co-glycolic acid) are uniformly or non-uniformly distributed in the microsphere By blending poly(propylene fumarate) into poly(lactic-co-glycolic acid) microspheres, the carbon-carbon double bonds of poly(propylene fumarate) can be used for covalent immobilization of these microspheres to a poly(propylene fumarate) containing scaffold, thus coupling microsphere release with poly(propylene fumarate) scaffold degradation. Preferably, the microsphere has a diameter in the range of 1 to 300 micrometers, and the microsphere has a surface free from indentations and cracks.

The bioactive agent is selected depending on the physiological effect desired. A "bioactive agent" as used herein includes without limitation physiologically or pharmacologically active substances that act locally or systemically in the body. A bioactive agent is a substance used for the treatment, prevention, diagnosis, cure or mitigation of disease or illness, or a substance which affects the structure or function of the body or which becomes biologically active or more active after it has been placed in a predetermined physiological environment. Bioactive agents include, without limitation, enzymes, organic catalysts, ribozymes, organometallics, proteins, glycoproteins, peptides, polyamino acids, antibodies, nucleic acids, steroidal molecules, antibiotics, antimycotics, cytokines, carbohydrates, oleophobics, lipids, extracellular matrix and/or its individual components, mammalian cells, genetically engineered cells, pharmaceuticals, and therapeutics. In bone tissue regeneration applications, example bioactive agents include, without limitation, growth factors such as transforming growth factor-beta (TGF-b), recombinant bone morphogenetic protein (BMP-2) and basic fibroblast growth factor (bFGF); peptides, growth hormones, osteoconductive agents; and cytokines. The bioactive agent is uniformly or non-uniformly dispersed in the microsphere, and the microsphere releases the bioactive agent in a sustained manner (and most preferably linear manner) after an initial burst release.

In a second aspect, the invention provides a crosslinkable, biodegradable material suitable for use as a replacement compound for living tissue, e.g., bone. "Biodegradable" means a material is capable of being degraded by biological processes such as enzymatic cleavage. In the material of the second aspect of the invention, the microspheres of the first aspect of the invention as described above can be incorporated into a flowable composition, along with poly (propylene fumarate) and a crosslinking agent for crosslinking the poly(propylene fumarate) in the scaffold to the poly(propylene fumarate) in the microspheres. The crosslinking may take place by way of a free radical initiator that adds to the carbon-carbon double bonds of the poly (propylene fumarate) to produce carbon radicals that further react with other carbon radicals formed. Example free radical initiators include, without limitation, benzoyl peroxide, azobisisobutyronitrile, and acetyl peroxide. The composition can be injected or inserted into skeletal defects of any size or shape.

Other additives can be incorporated into the crosslinkable, biodegradable material according the second aspect of the invention. A monomer capable of addition polymerization, such as vinyl pyrrolidone, acrylic acid, methyl methacrylate, styrene, methacrylic acid, or 2-hydroxy ethyl methacrylate, can be added to the material. Inorganic fillers, such as tricalcium phosphate and hydroxyapatite, can be added. A porogen, such as sodium chloride, may also be added. An accelerator, such as N,N dimethyl toluidine, can also be added to the material. The amounts of each optional additive may be varied according to the desired characteristics of the final composition.

In a third aspect, the invention provides a scaffold for tissue regeneration. The scaffold includes a poly(propylene fumarate) matrix having attached thereto the microspheres of the first aspect of the invention as described above. The microspheres are attached to the matrix by crosslinking between the poly(propylene fumarate) in the matrix and the poly(propylene fumarate) in the microspheres. The crosslinking may be achieved by way of a free radical initiator as described above. In one application, the scaffold is implanted in the body to provide a matrix for the ingrowth of new tissue and to provide for controlled release of the bioactive agent. As new tissue forms on the scaffold, the biomaterial degrades until it is entirely dissolved. At the same time, microsphere bioactive agent release is coupled with the poly(propylene fumarate) scaffold degradation.

EXAMPLES

The following Examples have been presented in order to further illustrate the invention and are not intended to limit the invention in any way. The Examples demonstrate that we have developed poly(propylene fumarate)/poly(lactic-co-glycolic acid) (PPF/PLGA) blend microspheres and have investigated the effects of various processing parameters on these microspheres. The advantage of these blend microspheres is that the carbon-carbon double bonds along the PPF backbone can be used for their immobilization in a PPF scaffold. Microspheres containing the model drug Texas red dextran were fabricated using a conventional double emulsion-solvent extraction technique. The effects of the following six processing parameters upon the microsphere characteristics were investigated: PPF/PLGA ratio, polymer viscosity, vortex speed, amount of internal aqueous phase, use of polyvinyl alcohol (PVA) in the internal aqueous phase and PVA concentration in the external aqueous phase.

The results show that the surface morphology was affected most by the viscosity of the polymer solution and showed an optimum kinematic viscosity of 39 centistokes. In most microsphere formulations, the model drug was dispersed uniformly in the polymer matrix. For all fabricated formulations, the microsphere diameter ranged between 1.7 and 298.8 micrometers. The external PVA concentration and the vortex speed had most effect on the size distribution. Entrapment efficiencies varied from 60.0 (±5.9)% to 98.0 (±2.4)% and was most effected by the amount of internal aqueous phase, vortex speed and polymer viscosity. Overall we demonstrated the ability of fabricating PPF/PLGA blend microspheres with similar surface morphology, entrapment efficiency and size distribution as conventional PLGA microspheres. We also proved uniform blending of PPF throughout the polymer matrix.

Example 1

A. Materials and Methods

1. Experimental Design

We investigated the effects of six fabrication parameters on the poly(propylene fumarate) (PPF)/poly(lactic-co-glycolic acid) (PLGA) microsphere characteristics. The parameters investigated were (1) PPF/PLGA ratio; (2) viscosity of polymer solutions; (3) vortex speed; (4) amount of internal phase (W1 phase); (5) poly(vinyl alcohol) (PVA) in internal water phase; (6) PVA amount in external water phase. As microsphere characteristics we investigated surface morphology, drug distribution, polymer blending, size distribution and entrapment efficiency of the model drug. The model drug Texas red dextran (Molecular Probes Inc., Leiden, The Netherlands) with a molecular weight of 40,000 Daltons was chosen for encapsulation to mimic the molecular weight of a bioactive protein. Prior to microsphere fabrication we quantified the viscosity of polymer solutions in fabrication circumstances.

The first part of the experiments was based on a Resolution III two-level factorial design varying all six parameters. (See, Box G, Hunter W, Hunter J S, "Statistics for Experimenters", New York: John Wiley & Sons, Inc. 1978.) High and low values were chosen for each parameter, and these levels were combined according to the fractional factorial design to create eight composite formulations. The values for all parameters are represented in Table 1. The effects of the six parameters on the surface morphology, the drug distribution, the drug entrapment efficiency and the size distribution of the microspheres were evaluated. The results from each experiment were examined to determine the main effects of each parameter on the measured property. The factorial design demonstrates the effect of each parameter on the measured microparticle characteristic while minimizing the number of trials.

The effects of PPF/PLGA ratio, polymer viscosity, vortex speed and amount of W1 phase were further studied in the second part of this study by increasing the range of these parameters. The effect of the PPF/PLGA ratio in the fabrication process was investigated by keeping the amount of polymer at 250 mg per ml of dichloromethane. The values for the fixed parameters are indicated in Table 1 except for the viscosity, which was kept at approximately 39 centistokes.

TABLE I (A) High and Low Levels for Parameters Tested in a Resolution
III, Two-Level Fractional Factorial Design

| Level | PPF/PLGA Ratio (%) | Polymer Viscosity (cSt) | Vortex Speed (**) | W1 Phase (µl) | Internal PVA (%) | External PVA (%) |
|---|---|---|---|---|---|---|
| + | 100/0 | 50 | 8 | 250 | 1% | 2% |
| − | 50/50* | 25 | 4* | 50* | 0* | 0.2% |

(B) Combinations of the Experimental Variables in the
Resolution III, Two-Level Fractional Factorial Design

| Formulations | PPF/PLGA Ratio | Polymer Viscosity | Vortex Speed | W1 Phase | Internal PVA | External PVA |
|---|---|---|---|---|---|---|
| 1 | + | + | + | + | + | + |
| 2 | + | + | − | + | − | − |
| 3 | + | − | + | − | + | − |
| 4 | + | − | − | − | − | + |
| 5 | − | + | + | − | − | + |
| 6 | − | + | − | − | + | − |
| 7 | − | − | + | + | − | − |
| 8 | − | − | − | + | + | + |

*Values in fabrication process used if parameters were isolated.
**Vortex Speed as indicated on Daigger Vortex Genie 2

All measurements were performed in triplicate and the data were expressed as means±standard deviations (SD), except for the main effects results where standard errors were reported.

2. Materials

Poly(lactic-co-glycolic acid) (Medisorb, Alkermes, Cincinnati, Ohio), with a 50:50 lactic to glycolic acid ratio and a weight-average molecular weight (Mw) of 46,000, was used for the microsphere preparation. Poly(propylene fumarate) (Cox Laboratory for Biomedical Engineering, Rice University, Houston, Tex.), with a number-average molecular weight (Mn) of 4,800 (Mw=8,236) was synthesized by a two-step reaction process as described by Peter et al. in "Synthesis of poly(propylene fumarate) by acylation of propylene glycol in the presence of a proton scavenger.", *J Biomater Sci Polym Ed* 1999;10:363–373. Poly(vinyl alcohol) (PVA, 87–89% mole hydrolyzed, Mw=13,000–23,000; Sigma) and isopropanol (IPA, 2-propanol, 99,5+% A.C.S. spectrophotometric grade; Aldrich Chemical Company) were used as purchased.

3. Viscosity Measurements

The kinematic viscosity of multiple concentrations of polymers dissolved in the organic solvent dichloromethane was measured using an Ubbelohde viscometer (International Research Glassware, Kenilworth, N.J.). The polymer solution, containing either pure PPF, a 50:50 ratio PPF/PLGA blend or pure PLGA dissolved in dichloromethane, was poured in the lower reservoir of the viscometer. The viscometer was placed vertically in a constant temperature bath at 20° C. for 20 minutes. The time for the meniscus to pass from one mark to another was measured. To measure the kinematic viscosity at different concentrations of polymer in the organic solvent, the polymer solution was diluted by addition of 1 ml of dichloromethane to the reservoir. Each time after dilution, the solution was vortexed and the measurement was repeated. To obtain the kinematic viscosity in centistokes, the efflux time in seconds was multiplied by the viscometer constant.

4. Microparticle Fabrication

A water-in-oil-in-water (W1-O-W2) double emulsion-solvent extraction technique was used for the preparation of the PPF/PLGA blended microspheres. (See, Lu et al., "Controlled release of transforming growth factor beta 1 from biodegradable polymer microparticles", *J Biomed Mater Res*, 50(3): 440–51, 2000; and Oldham et al., "Biological activity of rhBMP-2 released from PLGA microspheres", *J Biomech Eng.*, 122(3): 289–92, 2000.) Briefly, 500 mg of polymer was dissolved in dichloromethane in a glass test tube. While continuously vortexing (Daigger Vortex Genie 2, Fisher, Pittsburgh, Pa.) the polymer solution, 1.0 mg of Texas red dextran dissolved in a certain amount of distilled, deionized water was injected to create the first emulsion. The entire mixture was re-emulsified for 30 seconds in 4 ml of an aqueous PVA solution (w/v) to create the double emulsion. The content of the test tube was then poured into a 250 ml glass beaker containing 100 ml of a 0.3% aqueous PVA solution (w/v). The beaker was placed on a magnetic stirrer (Corning, Acton, Mass.) and 100 ml of a 2% isopropyl alcohol (IPA) aqueous solution (w/v) was added. The extraction of the dichloromethane to the external IPA aqueous phase resulted in precipitation of the dissolved polymers and subsequently the formation of the microspheres. After approximately 1 hr, the magnetic stirrer was removed from the mixture and the microparticles were given time to settle at the bottom. The supernatant was poured in a 50 ml centrifuge tube and centrifuged at 1000 rpm for 1 minute to collect the microspheres. After washing the microspheres twice with distilled, deionized water, they were placed at −20° C. for several hours and vacuum-dried (Savant Speedvac systems, Holbrook, N.Y.). This produced a free flowing powder that could be easily handled and stored at −20° C. prior to use.

5. Microparticle Characterization 5.1 Surface Morphology

The surface morphology of microspheres was observed by scanning electron microscopy (SEM) at 2 kV. Dry microspheres were mounted onto metal stubs using double-sided adhesive tape and sputter coated for 1 min. with a 1:1 ratio of gold and platinum. The particles were examined with a Hitachi S4700 Field Emission Scanning Microscope (SEM) (San Jose, Calif.) set at 2 kV.

5.2 Drug Distribution and Polymer Blending

A confocal laser-scanning microscope (Zeiss LSM510, Carl Zeiss, Germany), equipped with filters for 364 nm (Blue) and 543 nm (Red) excitation wavelengths was used to observe the drug (Texas red dextran) distribution within the microspheres and the polymer blending. Texas red dextran is fluorescent at 543 nm. By adjusting the wavelength, the filters and the pinhole, the presence of PPF could be shown since it is more blue fluorescent than PLGA. Dry microspheres were dispersed on cover-slips and representative fluorescence images of microparticle cross sections were taken through optical sectioning.

5.3 Size Distribution

The size distribution was determined by microsphere counts using the SEM pictures. The dimensions of microspheres and scale bar were measured on micrographs with a 100× and 300× magnification using CorelDRAW 8 (Corel, Ottawa, Ontario, Canada). The size distribution of the microspheres is expressed in average diameter.

5.4 Entrapment Efficiency

The entrapment efficiency of the model drug in the microspheres was determined by comparing the starting amount of Texas red dextran with the quantity contained by the microspheres after the double emulsion-solvent extraction technique. The Texas red dextran encapsulated in the microspheres was determined by dissolving 10 mg of microspheres in 1.5 ml of 1 M sodium hydroxide. The concentration of Texas red dextran was determined by absorption at 496 nm in a spectrophotometer (SpectraMax plus, Molecular Devices Corporation, Sunnyvale, Calif.). The background absorption at 496 nm of degradation products from PPF, PLGA and PPF/PLGA blend microspheres was measured by repeating this procedure using microspheres loaded with distilled, deionized water.

B. Results

1. Viscosity Measurements

Before starting the microsphere fabrication, the kinematic viscosity of the polymer solution was measured at increasing concentrations (FIG. 1). Our results demonstrated that a much higher concentration of PPF was needed to achieve the same viscosity as PLGA and small changes in PPF concentration resulted in less dramatic changes in viscosity compared to PLGA. The curve of the PPF/PLGA blend was between the two curves of the pure polymers.

2. Main Effects On Microsphere Characteristics

2.1. Surface Morphology

Figure 2:
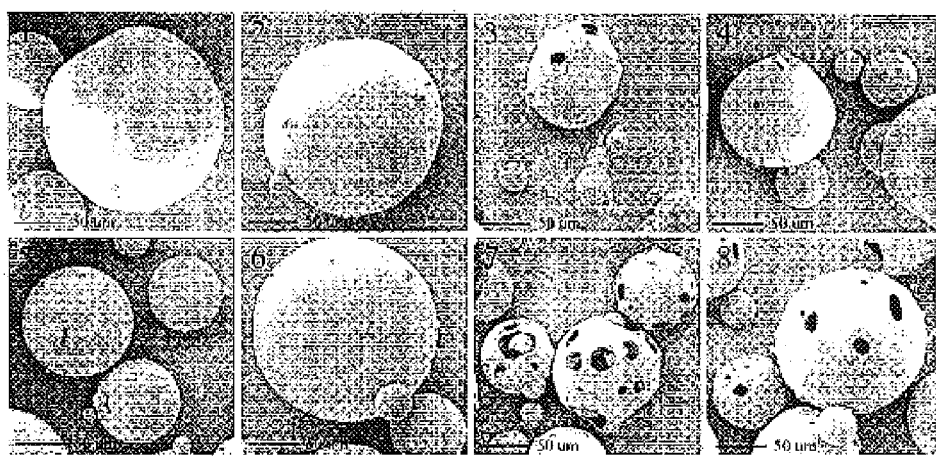
FIG. 2 shows SEM pictures showing the surface morphology of the 8 formulations of microspheres fabricated for the fractional factorial experimental design from which data in support of this application was gathered. The number of the picture corresponds to the formulation in Table 1B, which indicates the values used in the fabrication process.

Scanning electron microscopy revealed that microparticles were produced from all formulations (FIG. 2). There was a wide variation in cracks, dentations, porosity and surface smoothness between the different formulations. Overall, PPF/PLGA blend microspheres (5, 6, 7 and 8) had a smooth surface, whereas the ones made with pure PPF (1, 2, 3 and 4) had more dentations and cracks. Some of the PPF microspheres were broken open and revealed the inner honeycomb like structure. The majority of microspheres made with a low viscosity (formulations 3, 4, 7 and 8) had a very porous surface.

2.2. Drug Distribution

Figure 3:
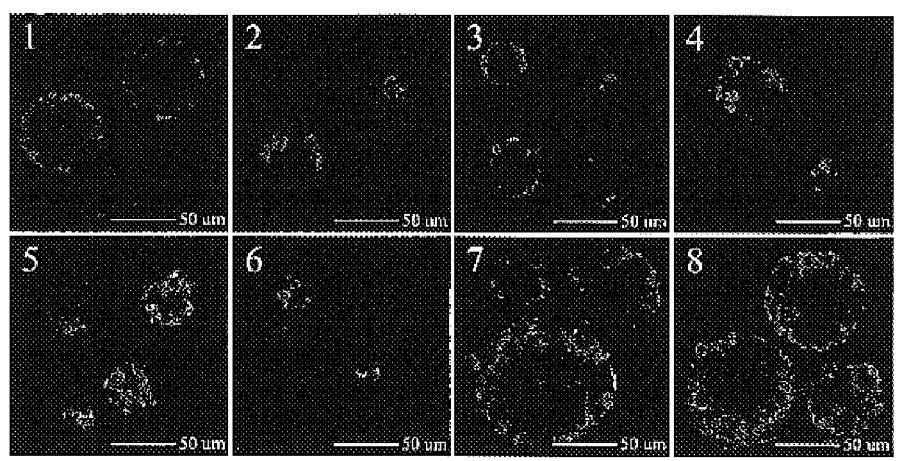
FIG. 3 shows confocal laser-scanning microscope (CLSM) images showing the distribution of Texas red dextran in the microspheres at an excitation wavelength of 543 nm. These are the 8 formulations fabricated for the fractional factorial design. The number of the picture corresponds to the formulation in Table 1B, which indicates the values used in the fabrication process.

Confocal light microscopy revealed that PPF was blended uniformly throughout the whole microsphere. Since the PPF was mixed uniformly through the microspheres the inner porous structure could be seen as well. The Texas red dextran was distributed uniformly in small drops through the polymer matrix within the microspheres (FIG. 3). Sometimes accumulations of dextran could be seen at or on the surface of the pores. With high amounts of W1 phase and internal PVA, the protein is distributed uniformly throughout the microspheres (formulations 1 and 8). When microspheres are produced with low levels of both parameters the dextran is more concentrated in drops (formulations 4 and 5).

2.3. Main Effects On Microparticle Size Distribution

Figure 4:
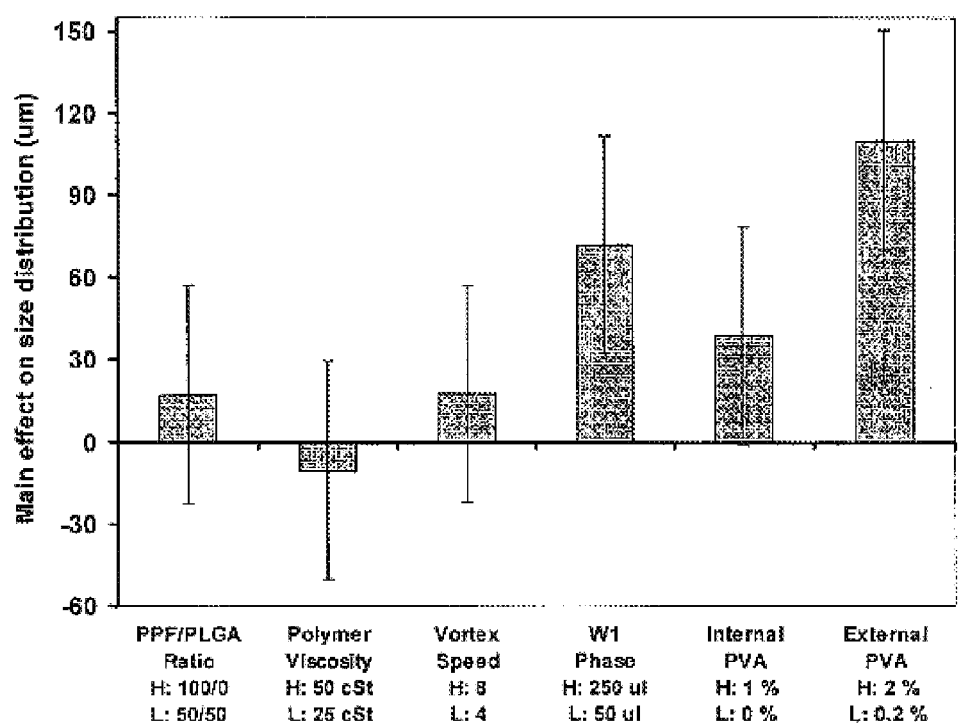
FIG. 4 shows the main effects of PPF/PLGA ratio, polymer viscosity, vortex speed, W1 phase, internal polyvinyl alcohol (PVA) and external PVA on the size distribution of the microspheres. A positive number indicates that the particular parameter had an increasing effect on the mean diameter of the microspheres as the value was changed from a low (L) level (−) to a high (H) level (+) (see Table 1A). A negative number indicates a decrease in mean microsphere diameter as the parameter was changed from a low (L) level (−) to a high (H) level (+). Error bars represent the standard errors of the effect.

For all formulations, microspheres were produced with a size varying between 1.7 and 197.8 micrometers. The size distribution for the different formulations is shown in Table 2. The microsphere size was most affected by the amount of W1 phase and the percent external (FIG. 4). Increasing the W1 phase and external PVA increased microsphere size. Varying all other parameters showed a minimal effect on microsphere size.

TABLE 2

Summary Of Results For The Entrapment Efficiency And Size Distribution Of Fractional Factorial Design

| Formulation | Entrapment Efficiency | Size Distribution |
|---|---|---|
| 1 | 88.6 ± 2.9 | 76.9 ± 64.1 |
| 2 | 71.9 ± 0.8 | 20.4 ± 33.3 |
| 3 | 80.4 ± 0.3 | 19.0 ± 21.7 |
| 4 | 72.7 ± 0.8 | 47.4 ± 48.6 |
| 5 | 76.9 ± 4.3 | 30.0 ± 32.6 |
| 6 | 72.7 ± 0.9 | 22.6 ± 31.9 |
| 7 | 91.6 ± 3.5 | 38.0 ± 36.2 |
| 8 | 87.7 ± 3.6 | 56.0 ± 50.4 |

2.4. Main Effects On Drug Entrapment Efficiency

Figure 5:
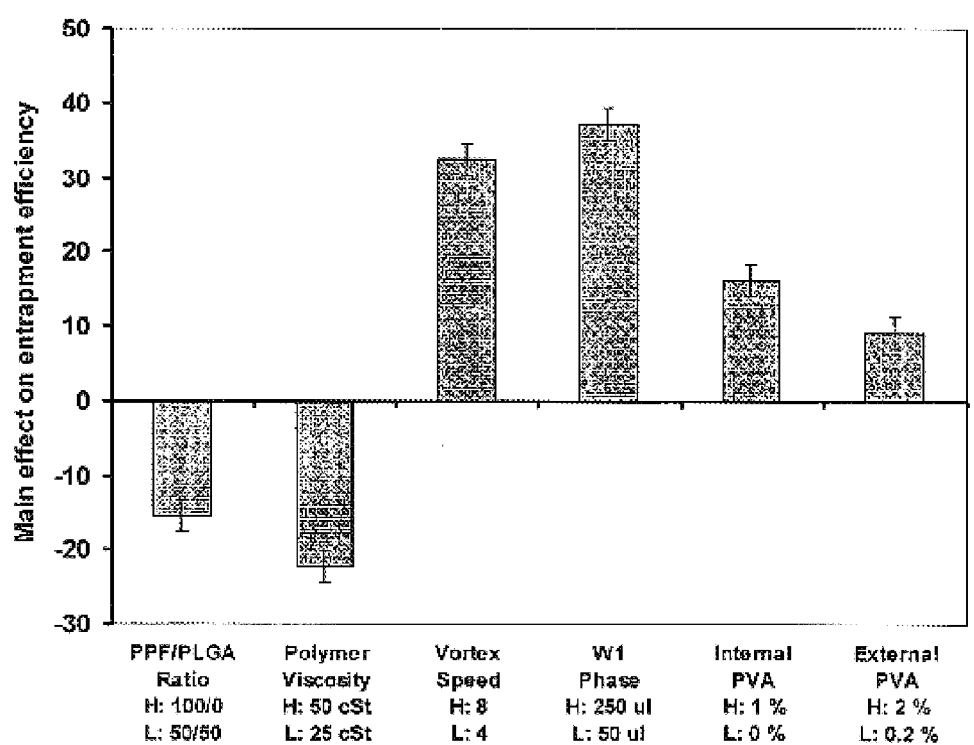
FIG. 5 shows the main effects of PPF/PLGA ratio, polymer viscosity, vortex speed, W1 phase, internal PVA and external PVA on the entrapment efficiency of the Texas red dextran. A positive number indicates that the particular parameter had an increasing effect on the entrapment efficiency of Texas red dextran as the value was changed from a low (L) level (−) to a high (H) level (+) (see Table 1A). A negative number indicates a decrease in entrapment efficiency of Texas red dextran as the parameter was changed from a low (L) level (−) to a high (H) level (+). Error bars represent the standard errors of the effect.

The entrapment efficiency of the microspheres showed a large variation for the different formulations ranging from 71.9 to 91.6% entrapped drug (Table 2). All parameters showed an effect on the entrapment efficiency (FIG. 5). The amount of first water phase containing the Texas red dextran had the highest effect. An increase in vortex speed, amount of first water phase, internal PVA and external PVA increased the amount of entrapped protein. In contrast, an increase in PPF in the polymer ratio and polymer viscosity decreased the entrapment efficiency (FIG. 5).

3. Effects Of PPF/PLGA Ratio

Figure 6:
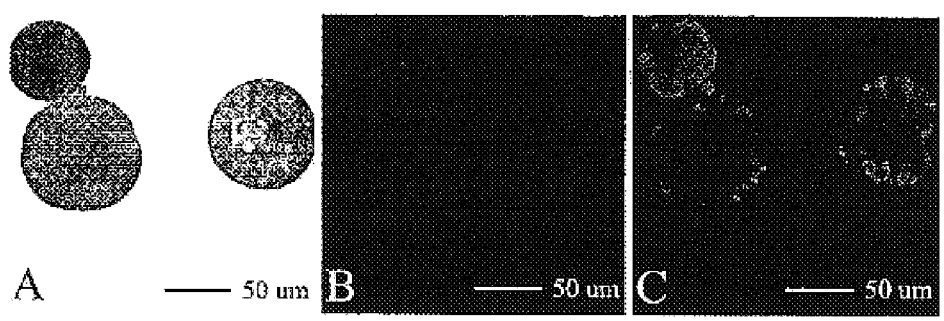
FIG. 6 shows CLSM images of a mixture of PPF and PLGA microspheres. The images originate from 1 picture that is split into (A) a light microscopy image, (B) the specific fluorescence at an excitation wavelength of 364 nm, and (C) the specific fluorescence at an excitation wavelength of 543 nm. In each image the microspheres on the left are PPF microspheres and show blue fluorescence in image B. The single microsphere on the right of each image is fabricated from PLGA and does not show the blue fluorescence in image B.

To evaluate the effect of incorporating PPF into microspheres during the fabrication process, 100, 75, 50, 25 and 0 percent of the weight of the PLGA was replaced by PPF in a constant amount of dichloromethane of 1 ml. The microspheres fabricated from PLGA had a smooth surface with very few pores. Raising the percentage of PPF resulted in an increasing irregularity and porosity of the surface and an increasing size of pores. Confocal light microscopy showed the model drug was distributed into small drops throughout the whole polymer mass and an increasing blue fluorescence as the percent PPF was raised (FIG. 6). The entrapment efficiency of the different formulations varied from 98.0% to 77.4% (Table 3). An increase in PPF in the polymer ratio decreased the average microsphere size (Table 3).

TABLE 3

Summary Of Results For The Entrapment Efficiency And Size Distribution Of PPF/PLGA Ratio

| Percent PPF | Entrapment Efficiency | Size Distribution |
|---|---|---|
| 0% | 98.0 ± 2.4 | 66.9 ± 29.2 |
| 25% | 77.4 ± 3.8 | 54.9 ± 24.6 |
| 50% | 86.5 ± 4.3 | 48.3 ± 27.0 |
| 75% | 94.4 ± 2.8 | 37.3 ± 23.9 |
| 100% | 84.9 ± 4.2 | 34.5 ± 21.4 |

4. Effects Of Polymer Viscosity

Figure 7:
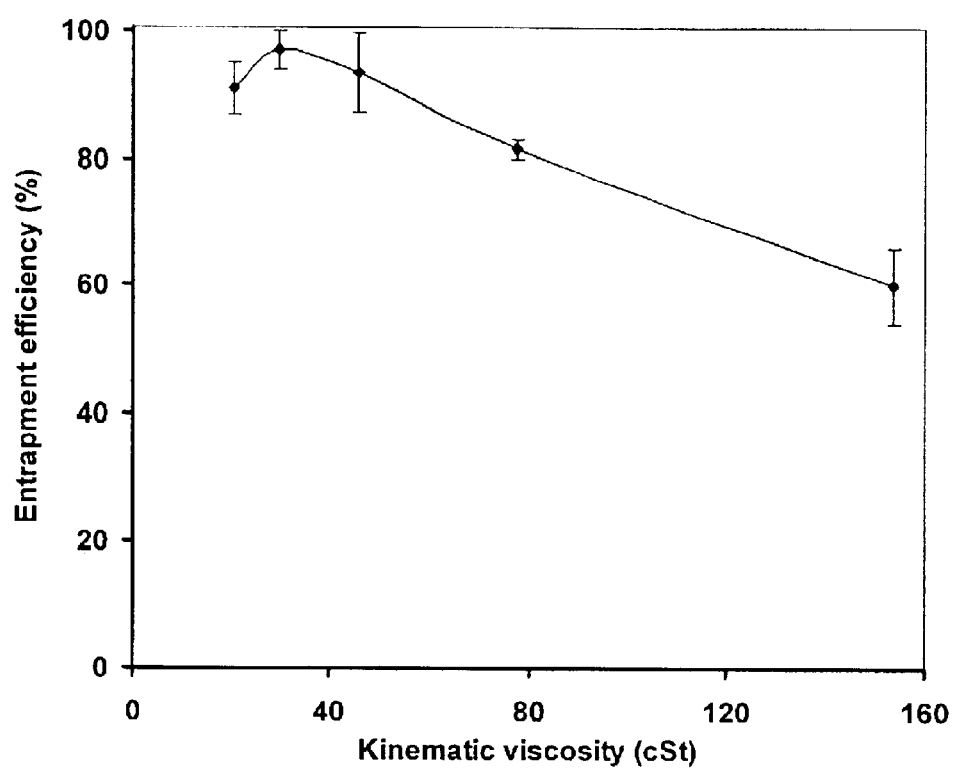
FIG. 7 shows the effect of the viscosity of the polymer solution on the entrapment efficiency of Texas red dextran within 50:50 PPF/PLGA blend microspheres.
Figure 8:
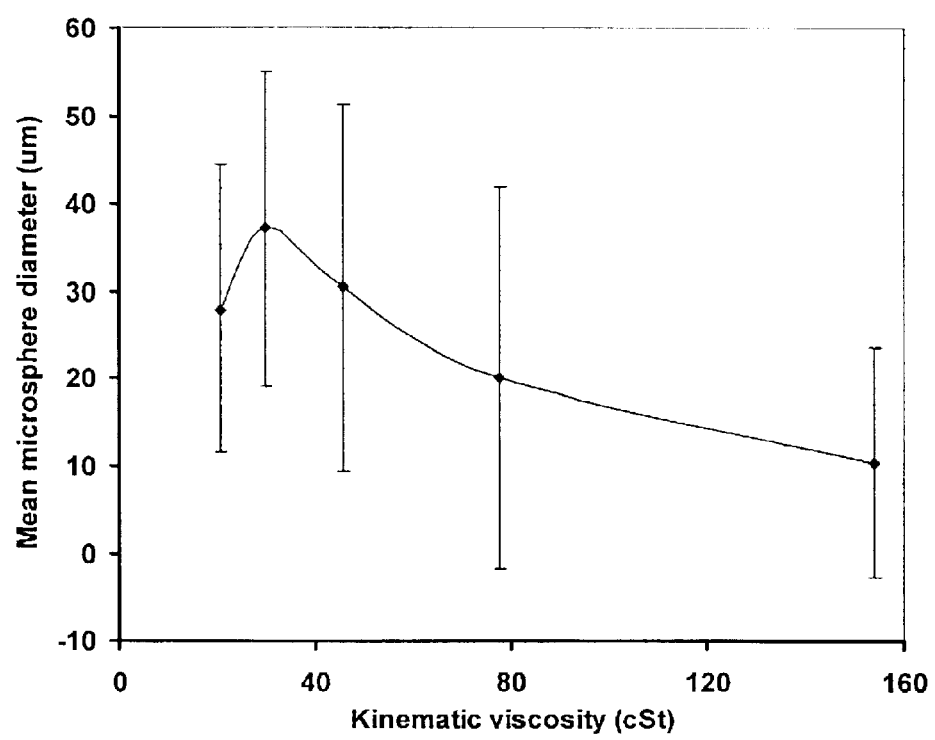
FIG. 8 shows the effect of the viscosity of the polymer solution on the average size of 50:50 PPF/PLGA blend microspheres.

Dissolving 500 mg of PPF/PLGA of a 50:50 ratio in 0.75, 1.00, 1.25, 1.50 and 1.75 ml of dichloromethane resulted in kinematic viscosities of 153.9, 77.7, 45.7, 29.7 and 20.6 centistokes of the oil phase. The microspheres created with a viscosity of 45.7 had a smooth surface with very few pores whereas those fabricated with higher or lower viscosities had porous surfaces. As shown in FIGS. 7 and 8 respectively, both entrapment efficiency and average size were maximized at a viscosity of 29.7 centistokes. Both the higher and lower viscosities had a lower entrapment efficiency and a lower size distribution.

5. Effects Of Vortex Speed

Figure 9:
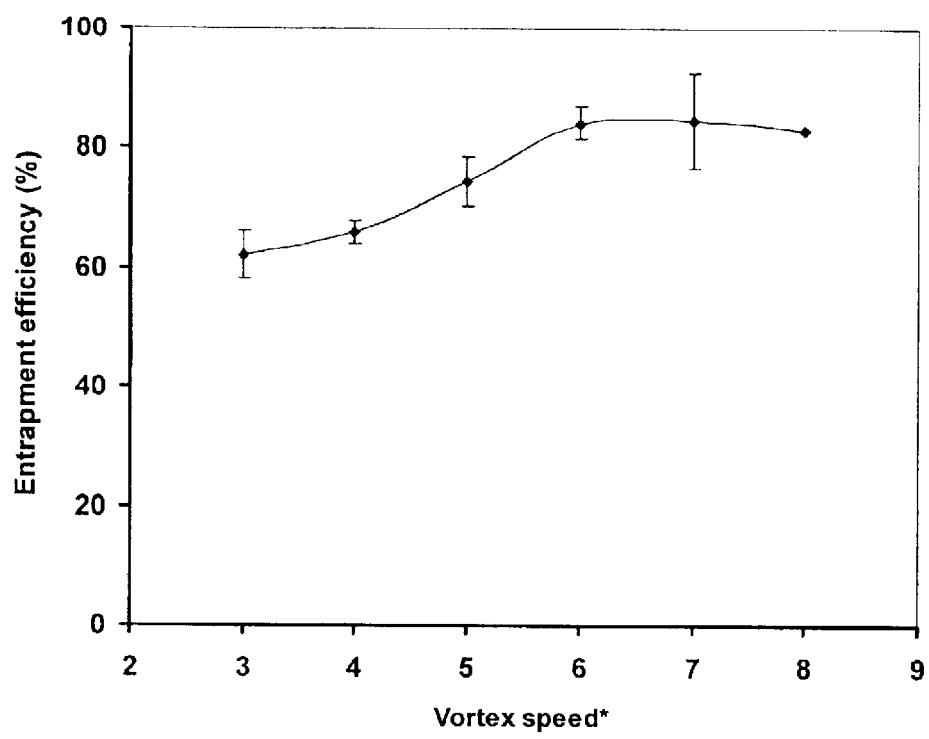
FIG. 9 shows the effect of vortex speed on the entrapment efficiency of Texas red dextran within 50:50 PPF/PLGA blend microspheres. Vortex settings 1, 2, 3, 4, 5, 6, 7, and 8 corresponded to 950, 1200, 1800, 2550, 2800, 2950, 3050, and 3150 revolutions per minute, respectively.
Figure 10:
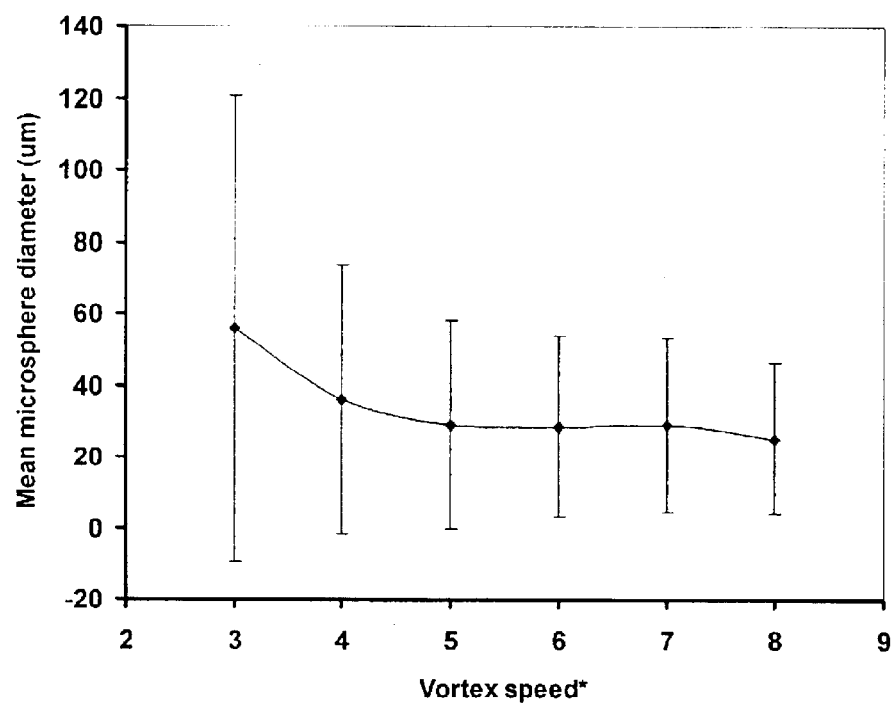
FIG. 10 shows the effect of vortex speed on the average size of 50:50 PPF/PLGA blend microspheres. Vortex settings 1, 2, 3, 4, 5, 6, 7, and 8 corresponded to 950, 1200, 1800, 2550, 2800, 2950, 3050, and 3150 revolutions per minute, respectively.

For studying the effects of the vortex speed, the concentration was kept at the same level as the commonly used PLGA polymer solution (250 mg/ml). Scanning electron micrographs revealed that all microspheres had a smooth surface regardless of what vortex speed was used. The entrapment efficiency of the model drug in the microspheres showed an increase as the vortex speed increased (FIG. 9). An increase in vortex speed not only resulted in a decrease in average microsphere size but also in a more narrow distribution in sizes (FIG. 10). At a vortex speed of 3, the microsphere size varied form 5.2 to 370.1 μm, which narrowed down to sizes between 2.1 and 90.5 μm at a vortex speed of 8.

6. Effects Of Internal Aqueous Phase Amounts

To study the effect of the amount of internal aqueous phase, microspheres were fabricated using 50, 150, 250, 350 and 450 microliters of aqueous phase containing 0.5 mg of Texas red dextran. All microspheres were spherical with a smooth surface. No distinct difference in surface morphology could be seen on the SEM pictures. Increasing the amount of internal aqueous phase resulted in a slight increase in average size (Table 4). The entrapment efficiency also initially increased as more aqueous phase was used. However, raising it from 150 microliters the trend changed to a decrease in encapsulated model drug (Table 4).

TABLE 4

Summary Of Results For The Entrapment Efficiency And Size Distribution Of W1 Phase

| W1 Phase | Entrapment Efficiency | Size Distribution |
|---|---|---|
| 50 (μl) | 80.7 ± 6.9 | 20.5 ± 20.6 |
| 150 (μl) | 87.5 ± 6.9 | 33.0 ± 24.8 |
| 250 (μl) | 78.2 ± 5.9 | 31.2 ± 26.5 |
| 350 (μl) | 68.2 ± 7.0 | 25.3 ± 26.3 |
| 450 (μl) | 66.0 ± 9.4 | 25.2 ± 22.5 |

C. Discussion

In the present study, we demonstrated that biodegradable PPF/PLGA blend microspheres loaded with the model drug Texas red dextran can be fabricated using the established double emulsion-solvent extraction technique. The first part of the experiments, using the fractional factorial design, was designed to determine the effects of the different processing parameters on the microsphere characteristics. In the second part we investigated some individual parameters to gather more detailed information on the fabrication process. Even though we did not investigate all possible processing parameter combinations, this study gives adequate insight in the process to fabricate PPF/PLGA blend microspheres. We demonstrated the ability of fabricating PPF/PLGA blend microspheres with similar surface morphology, entrapment efficiency and size distribution as PLGA microspheres.

Surface morphology is an important microsphere characteristic since release of an encapsulated drug is expected to depend on it. In the present study, the viscosity was the most important factor affecting the surface porosity. At a viscosity of approximately 39 centistokes, the PPF/PLGA blend microspheres and the pure PLGA microspheres had similar smooth surface morphologies. Since the initial viscosity measurements indicated that PPF and PLGA solutions had different characteristics, it is not surprising that the concentration of the polymer solution needs to be adjusted for different PPF/PLGA blend ratios in order to obtain the same viscosity, thus a similar surface morphology after microsphere fabrication.

Key factors known to influence the size of microspheres are PVA concentration in external water phase, stirring speed and viscosity of the polymer solution. (See, Davis et al., "The preparation and characterization of poly(lactic-co-glycolide) microparticles. I. Oil-in-water emulsion solvent evaporation.", *Int J Pharm.*, 1991;77:169–75; Davis et al., "The preparation and characterization of poly(lactic-co-glycolide) microparticles. II. The entrapment of a model protein using a (water in oil)-in-water emulsion solvent evaporation technique.", *Pharm Res*, 1993;10:362–8; Crotts et al., "Preparation of porous and nonporous biodegradable polymeric hollow microspheres.", *J Control Rel.*, 1995;35:91–105; and Roy et al., "Indomethacin-loaded microspheres: design and preparation by a multiple-emulsification technique and their in vitro evaluation.", *Pharm Res.*, 1992;9:1132–6). Since PVA is a polymer with a high molecular weight, the presence of PVA in the external water phase may increase the viscosity of the double emulsion, resulting in an increasing difficulty in breaking up the emulsion into smaller droplets. (See, Yang et al., "Morphology, drug distribution, and in vitro release of biodegradable polymeric microspheres containing protein fabricated by double-emulsion solvent extraction/evaporation method.", *Biomaterials*, 2001-;22:231–41.) This results in bigger microspheres. The stirring speed is mostly described as the dominating factor in size distribution since it provides the energy to disperse the oil phase in the external aqueous phase. (See, Yang et al. above.) High stirring speed yields smaller microspheres because the second water emulsion is broken up into smaller droplets at a higher input power. The narrower distribution at increased vortex speeds is likely caused by a minimum drop size impossible of breaking up further. Breaking up the polymer solution into smaller droplets is easier at lower polymer solution viscosities. If the viscosity of the polymer solution is increased, the difficulty of cutting through the droplets increases. This results in tearing of small parts causing a wider distribution with a lot of very small particles and some very large particles.

Entrapment efficiency is an important microsphere characteristic for economic reasons. All parameters had their distinct effect on the entrapment efficiency. Poly(vinyl alcohol), used as an emulsifier, helps to stabilize the emulsions, thereby preventing mass transfer of the drug with the surroundings and resulting in higher entrapment efficiencies. The vortex speed provides the energy for the dispersion of the aqueous drug solution into the oil phase. A fine dispersion results in high entrapment efficiency. (See, Bodemeier, "Encapsulation of water soluble drugs by a solvent evaporation method. I. Effects of process and formulation variables on drug entrapment." *J. Microencapsulation* 1990;7(3):347–355.) The effect of amount of W1 phase is determined by two mechanisms resulting in an optimum percentage of entrapped drug. Since low amounts result in a more concentrated drug solution, the entrapment efficiency decreases because of drug diffusion controlled by an increasing concentration gradient. (See, Yang et al. above.) At higher aqueous loadings the entrapment efficiency drops as well because the increasing proportion of droplets at the surface of the emulsion enhances drug loss to the external water phase.

Another parameter which affects optimal entrapment efficiency is polymer solution viscosity. The organic solution serves as a diffusion barrier for the drug between the two aqueous phases. Drug loss is low as long as organic solvent is present but increases once solvent is evaporated. At high viscosities, polymer precipitation occurs much earlier resulting in lower entrapment efficiencies because of more diffusion. (See, Bodemeier et al., "Solvent selection in the preparation of poly(DL-lactide) microspheres prepared by the solvent evaporation method.", *Int. J. Pharm* 1988;43:179–186; and Schugens et al., "Effects of the emulsion stability on the morphology and porosity of semi-crystalline poly L-lactide microspheres prepared by W-O-W double emulsion-evaporation.", *J Controlled Release* 1994;32:161–176.) At low viscosities the double emulsion is less stable. The high surface energy of water (72.8 mJ/m$^2$) causes internal water droplets to coalesce and mix with the external aqueous phase. (See, Yang et al. and Bodemeier above.)

The most important characteristic of this study was the polymer blending within the microspheres. The carbon-carbon double bonds along the PPF backbone will be used for immobilizing the microspheres in a PPF scaffold, which requires a uniform blending of the polymers. Since our results show PPF is blended uniformly throughout the polymer matrix, it is expected that PPF molecules are present at the microsphere surface. This can give the PPF/PLGA blend microspheres a unique binding capacity.

Example 2

A. Materials and Methods

Blend microspheres of poly(propylene fumarate) (PPF) (Mn 4800) and poly(lactic-co-glycolic acid) (PLGA) (Mw 50,000) containing 0, 25, 50, 75 and 100 percent PPF were fabricated using an established water-in-oil-in-water (W1-O-W2) technique (see, S. J. Peter et al. "Effects of transforming growth factor β1 released from biodegradable polymer microparticles on marrow stomal osteoblasts cultured on poly(propylene fumarate) substrates", *J. Biomed Mater Res.* 50: 452–62, 2000). Briefly, while continuously vortexing a polymer solution in $CH_2Cl_2$, an aqueous solution containing 500 µg Texas red-dextran (Mw 40,000) as a model drug was injected to create the first emulsion. The entire mixture was re-emulsified in a poly(vinyl alcohol) (PVA) solution. The double emulsion was poured into a beaker containing an isopropanol (IPA) solution and stirred. The evaporation of the $CH_2Cl_2$ resulted in precipitation of the dissolved polymers and subsequent formation of the microspheres. The microspheres were washed, vacuum-dried and stored at −20° C. until use.

The effects of various processing parameters on the morphology, size distribution and drug entrapment efficiency were investigated. We varied the vortex speed (2, 4, 6), the amount of the W1 phase (50, 100, 150 µl), the stirring time (1, 18 hours), and temperature during stirring (25° C., 40° C.).

The percentage of Texas red-dextran encapsulated in the microspheres was determined by normalizing the amount actually entrapped to the starting amount. Approximately 15 mg of microspheres was dissolved in 1.5 ml of 1 M sodium hydroxide and concentration of dextran was measured by absorption at 595 nm.

2. Results and Discussion

Figure 11:
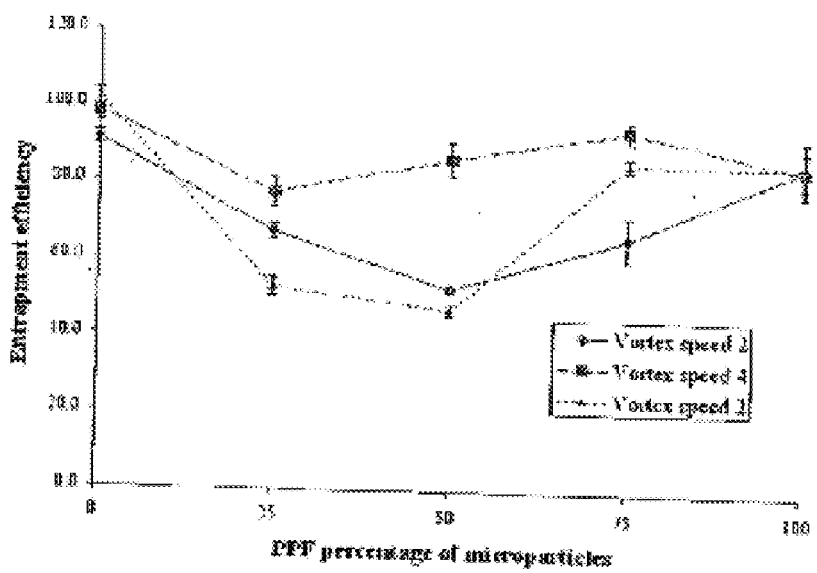
FIG. 11 shows the entrapment efficiency of dextran in PPF/PLGA blend microspheres fabricated at different vortex speeds. Vortex settings 1, 2, 3, 4, 5, 6, 7, and 8 corresponded to 950, 1200, 1800, 2550, 2800, 2950, 3050, and 3150 revolutions per minute, respectively.

Using the W1-O-W2 technique, PPF/PLGA microspheres containing 0, 25, 50, 75, 100 percent PPF were fabricated. The processing parameters in the fabrication process were shown to affect the morphology, size distribution and drug entrapment efficiency. For example, increasing the amount of W1 phase in the manufacturing process using a low concentration polymer solution resulted in decreased entrapment efficiency. For all compositions studied with a low concentration of polymer solution, higher entrapment efficiency was achieved using an intermediate vortex speed (see FIG. 11).

Figure 12:
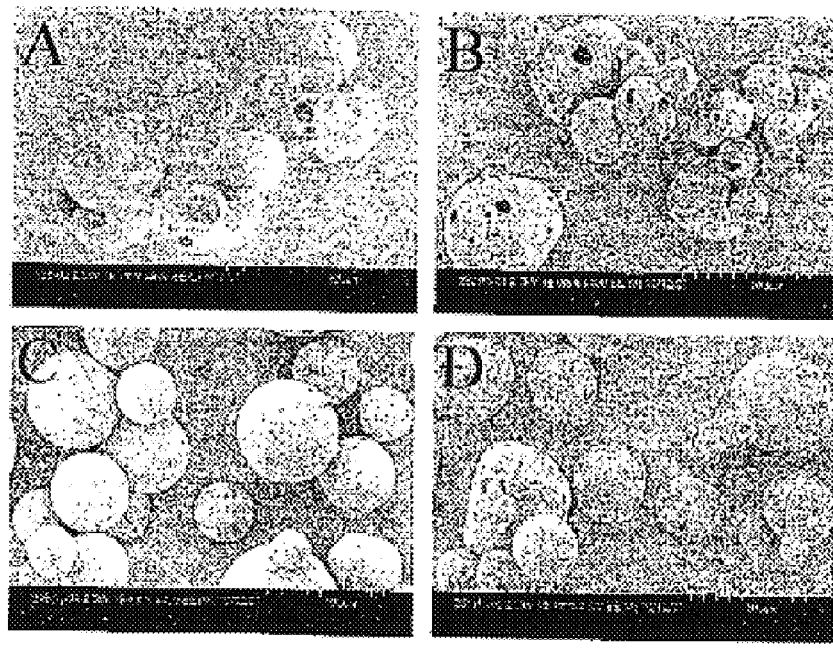
FIG. 12 shows SEM pictures of microparticles containing 50% PPF fabricated using low (A,B) and high (C,D) polymer concentrations. The stirring time and temperature were 1 hour at 25° C. (A,C), 1 hour at 40° C. (B), and 18 hour at 25° C. (D).

Most of the microspheres were 10 to 120 µm in diameter. Parameters that had the most effect on the size distribution were the vortex speed and polymer concentration. Fewer micropores were observed in microspheres fabricated with a higher concentration of the polymer solution. SEM pictures also demonstrated that stirring conditions had an effect on the surface morphology (see FIG. 12).

Our results show that blended microspheres with different ratios of PPF and PLGA can be manufactured and loaded with Texas red-dextran as a model drug. Important processing parameters were identified that affect the surface morphology, size distribution and drug entrapment efficiency of the microspheres.

Example 3

A. Materials and Methods

Microspheres of pure PPF (Mn 4800), blended PPF/PLGA (ratios: 75/25, 50/50, 25/75) and pure PLGA (Mw 50,000) were fabricated using a conventional double emulsion solvent extraction technique (see, J. B. Oldham, et al, "Biological activity of rhBMP-2 released from PLGA microspheres", *J. Biomech. Eng.* 122: 289–292, 2000). Texas red-dextran (Mw 40,000 Molecular Probes Inc.), was encapsulated as a modal drug. After fabrication, we characterized the microspheres by examining the surface morphology using scanning electron microscopy (SEM), the size distribution (Coulter Multisizer III), and entrapment efficiencies of the encapsulated molecules. The distribution of Texas red-dextran within the microspheres was visualized by confocal microscopy.

To study the release kinetics, approximately 25 mg of microparticles were placed in micro-centrifuge tubes containing 1 ml of phosphate buffered saline (PBS). At 0.25, 0.5, 1, 2, 3, 4, 5, 7, 10, 14, 16, 19, 23, 28 days the supernatant was collected for analysis. The amount of Texas red-dextran released was measured at 595 nm using a spectrophotometer.

The degradation of the microspheres was studied under the same conditions as the protein release experiment. At days 14 and 28, surface morphologies were studied by SEM. The molecular weight distribution of the degrading polymers was analyzed by gel permeation chromatography.

B. Results and Discussion

Figure 13:
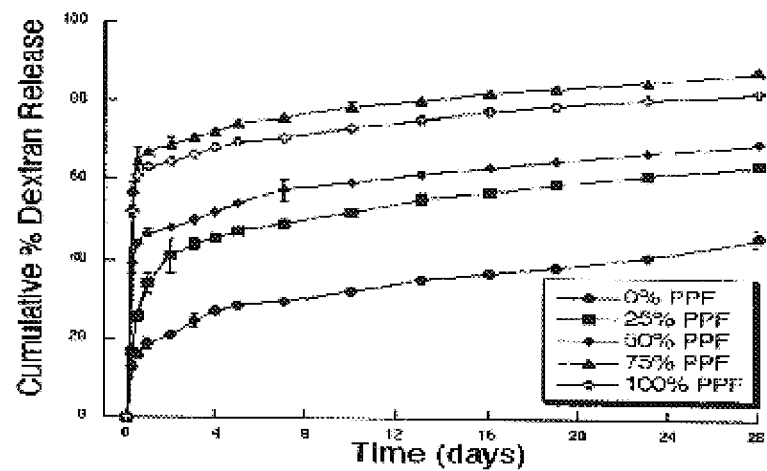
FIG. 13 shows the effects of PPF/PLGA ratio on cumulative release of co-encapsulated Texas Red dextran.

The fabricated microspheres had an entrapment efficiency varying from 77.4% to 98.0%, which was not dependent upon the PPF ratio. A 28-day release study showed that all microparticles had a similar release profile. With an exception of 100% PPF the initial burst release of the co-encapsulated Texas red-dextran increased with increasing PPF (FIG. 13). This was probably because with increasing the ratio of PPF the particles had more pores after fabrication and thus a larger surface area. Furthermore, the microspheres released the bioactive agent in a linear manner after an initial burst release.

Figure 14:
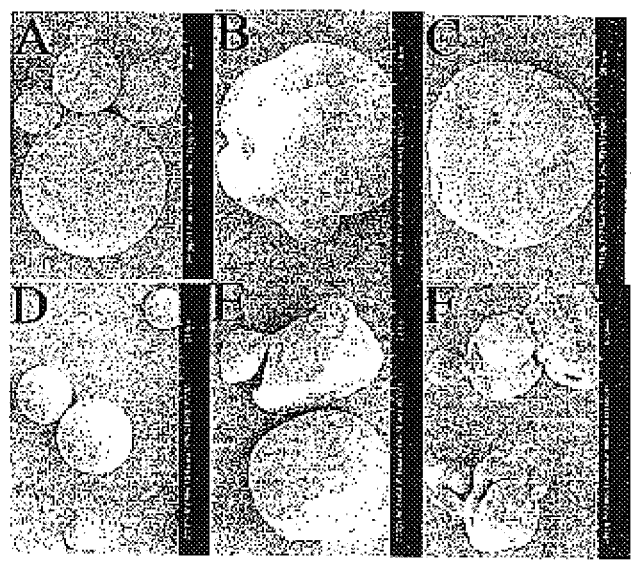
FIG. 14 shows scanning electron micrographs of PLGA (A,B,C) and PPF (D,E,F) microparticles at day 0 (left), day 14 (middle) and day 28 (right).

SEM pictures showed that all microparticles initially had a spherical shape but those containing PPF had some pores in the surface (FIG. 14). During degradation all microspheres became irregularly shaped and those containing PPF had a tendency to aggregate. With an increasing amount of PPF within the spheres there were less new micropores formed during degradation.

Thus, Texas red-dextran was entrapped at high efficiencies in the PPF/PLGA blend microspheres and was released in a controlled manner. These biodegradable microspheres may serve as vehicles for the controlled delivery of bioactive molecules.

Although the present invention has been described in considerable detail with reference to certain embodiments of blend, cross-linkable poly(propylene fumarate) for immobilization and controlled drug delivery, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A microsphere for controlled release of a bioactive agent, the microsphere comprising:

poly(propylene fumarate);

a polymeric material other than poly(propylene fumarate); and a bioactive agent.

2. The microsphere of claim 1 wherein:

the polymeric material is poly(lactic-co-glycolic acid).

3. The microsphere of claim 2 wherein:

the bioactive agent is selected from osteoinductive agents, peptides, growth hormones, osteoconductive agents, cytokines and mixtures thereof.

4. The microsphere of claim 2 wherein:

the bioactive agent comprises a bone morphogenetic protein.

5. The material of claim 2 wherein:

the bioactive agent is selected from cytokines and growth factors.

6. The microsphere of claim 2 wherein:

the bioactive agent is uniformly dispersed in the microsphere.

7. The microsphere of claim 2 wherein:

the bioactive agent is non-uniformly dispersed in the microsphere.

8. The microsphere of claim 2 wherein:

the microsphere has a diameter in the range of 1 to 300 micrometers.

9. The microsphere of claim 2 wherein:

the poly(propylene fumarate) and poly(lactic-co-glycolic acid) are uniformly distributed in the microsphere.

10. The microsphere of claim 2 wherein:

the poly(propylene fumarate) and poly(lactic-co-glycolic acid) are non-uniformly distributed in the microsphere.

11. The microsphere of claim 2 wherein:

the microsphere releases the bioactive agent in a sustained manner after an initial burst release.

12. A crosslinkable, biodegradable material comprising:

a first polymeric material;

microspheres comprising the first polymeric material, a second polymeric material, and a bioactive agent; and a crosslinking agent for crosslinking the first polymeric material.

13. The material of claim 12 wherein:

the first polymeric material is poly(propylene fumarate).

14. The material of claim 13 wherein:

the second polymeric material is poly(lactic-co-glycolic acid).

15. The material of claim 13 wherein:

wherein the material is injectable.

16. The material of claim 13 wherein:

the crosslinking agent is a free radical initiator.

17. The material of claim 13 wherein:

the bioactive agent is selected from osteoinductive agents, peptides, growth hormones, osteoconductive agents, cytokines and mixtures thereof.

18. The material of claim 14 wherein:

the poly(propylene fumarate) and poly(lactic-co-glycolic acid) are uniformly distributed in the microsphere.

19. The material of claim 14 wherein:

the poly(propylene fumarate) and poly(lactic-co-glycolic acid) are non-uniformly distributed in the microsphere.

20. The material of claim 12 wherein:

the first polymeric material includes a double bond.

21. A scaffold for tissue regeneration, the scaffold comprising:

a biodegradable matrix comprising a first polymeric material; and a microsphere comprising the first polymeric material, a second polymeric material, and a bioactive agent, wherein at least a portion of the first polymeric material in the matrix and at least a portion of the first polymeric material in the microsphere are crosslinked.

22. The scaffold of claim 21 wherein:

the first polymeric material is poly(propylene fumarate).

23. The scaffold of claim 22 wherein:

the second polymeric material is poly(lactic-co-glycolic acid).

24. The scaffold of claim 23 wherein:

the tissue is bone.

25. The scaffold of claim 24 wherein:

the bioactive agent is selected from osteoinductive agents, peptides, growth hormones, osteoconductive agents, cytokines and mixtures thereof.

26. The scaffold of claim 23 wherein:

the poly(propylene fumarate) and poly(lactic-co-glycolic acid) are uniformly distributed in the microsphere.

27. The scaffold of claim 23 wherein:

the poly(propylene fumarate) and poly(lactic-co-glycolic acid) are non-uniformly distributed in the microsphere.

* * * * *